US008845709B2

(12) United States Patent
Styrc et al.

(10) Patent No.: US 8,845,709 B2
(45) Date of Patent: Sep. 30, 2014

(54) DEVICE FOR TREATING A BLOOD VESSEL

(75) Inventors: Mikolaj Witold Styrc, Kopstal (LU); Ning Wen, Chantilly (FR); Eric Perouse, Paris (FR)

(73) Assignee: Laboratories Perouse, Ivry le Temple (FR)

( * ) Notice: Subject to any disclaimer, the term of this patent is extended or adjusted under 35 U.S.C. 154(b) by 1578 days.

(21) Appl. No.: 11/922,237

(22) PCT Filed: Jun. 12, 2006

(86) PCT No.: PCT/FR2006/001321
§ 371 (c)(1),
(2), (4) Date: Sep. 24, 2009

(87) PCT Pub. No.: WO2006/134258
PCT Pub. Date: Dec. 21, 2006

(65) Prior Publication Data
US 2010/0016944 A1    Jan. 21, 2010

(30) Foreign Application Priority Data
Jun. 15, 2005    (FR) .................................. 05 06081

(51) Int. Cl.
*A61F 2/06*    (2013.01)
*A61F 2/95*    (2013.01)
(52) U.S. Cl.
CPC ........... *A61F 2/95* (2013.01); *A61F 2002/9517* (2013.01); *A61F 2002/9511* (2013.01); *A61F 2002/9505* (2013.01)
USPC .................................................... 623/1.11
(58) Field of Classification Search
USPC .............. 623/1.11–1.12, 1.23, 2.11; 606/108; 600/585
See application file for complete search history.

(56) References Cited

U.S. PATENT DOCUMENTS 6,302,891 B1 * 10/2001 Nadal ............................ 606/108
6,740,111 B1 * 5/2004 Lauterjung .................... 623/1.1
6,764,503 B1 * 7/2004 Ishimaru ...................... 623/1.11
(Continued)

FOREIGN PATENT DOCUMENTS

FR    2 688 688        9/1993
FR    2 863 160        6/2005
FR    2 865 926        8/2005
FR       2865926 A1 *  8/2005   ................ A61F 2/06

OTHER PUBLICATIONS

International Search Report issued Nov. 2, 2006 in the International (PCT) Application of which the present application is the U.S. National Stage.

*Primary Examiner* — Darwin Erezo
*Assistant Examiner* — Amy Shipley
(74) *Attorney, Agent, or Firm* — Wenderoth, Lind & Ponack, L.L.P.

(57) ABSTRACT

A device includes an expandable implant and a hollow stent internally defining a central passage. The hollow stent defines a retention opening of the implant near the distal end thereof. The inventive device also includes a wire-type link for releasably fixing the implant to the stent, which has a traction section introduced into the opening and extending inside the central passage. For the wire-type link, the device includes an internal insulation channel arranged in the central passage and axially fixed with respect to the stent. The insulation channel receives only one wire-type link and defines a channel which is devoid of a link at least between the proximal end of the stent and the retention opening and is placed in the central channel.

16 Claims, 6 Drawing Sheets

(56) References Cited

U.S. PATENT DOCUMENTS

| | | | |
|---|---|---|---|
| 7,537,606 B2 * | 5/2009 | Hartley et al. | 623/1.11 |
| 7,867,270 B2 * | 1/2011 | Hartley et al. | 623/1.11 |
| 7,993,383 B2 * | 8/2011 | Hartley et al. | 623/1.11 |
| 2003/0004560 A1 | 1/2003 | Chobotov et al. | |
| 2004/0193252 A1 * | 9/2004 | Perez et al. | 623/1.23 |
| 2005/0119722 A1 | 6/2005 | Styrc et al. | |
| 2007/0043432 A1 * | 2/2007 | Perouse | 623/1.36 |
| 2008/0228255 A1 * | 9/2008 | Rust et al. | 623/1.11 |
| 2008/0234797 A1 * | 9/2008 | Styrc | 623/1.11 |
| 2010/0268322 A1 * | 10/2010 | Styrc et al. | 623/1.15 |

* cited by examiner

DEVICE FOR TREATING A BLOOD VESSEL

This application is a 371 of PCT/FR2006/001321 filed on Jun. 12, 2006, which draws priority from France 0506081 filed on Jun. 15, 2005.

BACKGROUND OF THE INVENTION

The present invention relates to device for treating a blood vessel comprising at least one implant, deployable between a contracted state and an expanded state. A hollow prop internally delimits a central passage between a proximal end and a distal end, and in the vicinity of its distal end, the hollow prop defines defining at least one opening for retaining the implant. At least one filamentary line releasably fixes the implant to the prop, and each filamentary line comprises a pulling portion engaged in the opening and extending into the central passage at least as far as a control end which can be operated from the proximal end of the prop.

A device of this type is used for releasing implants into a blood vessel, such as tubular endoprostheses usually referred to as "stents" or other types of endoprostheses, such as endo-valves.

A device of the aforementioned type is disclosed in FR-A-2 863 160. In this device, an endoprosthesis is mounted coaxially on a hollow prop. The endoprosthesis is held in its refracted state with the aid of two filamentary lines which surround the endoprosthesis at its ends. The filamentary lines are respectively engaged in the distal and proximal retaining openings provided in the prop. Each filamentary line comprises a control portion which extends into the prop as far as a respective control end accessible to the user through a respective lateral branch of the prop. In this device, each end of the endoprosthesis can be released independently of the other end. Thus, the control portion of one of the filamentary lines is displaced inside the prop towards the distal end so as to disengage the corresponding end of the endoprosthesis. The filamentary line is then extracted from the device when the endoprosthesis has been satisfactorily placed in the vessel.

A surgical guide is pre-positioned in the blood vessel in order to insert the device into the patient's blood vessel. Next, the prop bearing the endoprosthesis is inserted into the vessel by being slid along the guide. During this insertion, or during the subsequent movement of the filamentary lines, the lines and the guide may become entangled, which adversely affects the reliability of the device.

SUMMARY OF THE INVENTION

An object of the invention is therefore to provide a device for treating a blood vessel which can be precisely positioned in the vessel and which has improved reliability. For each filamentary line, the device comprises an internal insulating duct provided in the central passage and axially fixed with respect to the prop, and each insulating duct receives only one line and delimits, in the central passage, a guiding duct with no line at least between the proximal end of the prop and a retaining opening.

The device according to the invention may comprise one or more of the following features taken in isolation or in any technically feasible combination.

Each insulating duct can delimit a channel for receiving the line extending in cross-section over part of a circumference surrounding a longitudinal axis of the central passage.

Each insulating duct can have a distal passage extending substantially opposite an associated retaining opening, each line being engaged in the distal passage.

Each insulating duct can have a distal end sealed in a bevelled manner.

Each insulating duct can be engaged in the retaining opening and can comprise a collar disposed on an external surface of the prop, the collar delimiting the distal passage.

Each insulating duct can be integral with the prop substantially along the entire length of the insulating duct, or each insulating duct can be integral with the prop.

The prop can comprise a proximal passage opening and a distal passage opening which are substantially coaxial. The guiding duct with no line extends between the openings and is delimited, in the vicinity of at least one of the passage openings, by a distally diverging surface.

The device can comprise at least two filamentary lines, the insulating ducts associated with at least two lines being arranged on the periphery of the guiding duct with no line.

The device can comprise only one prop, at least two longitudinally spaced retaining openings being provided in the prop.

The device can comprise an element for joint movement of at least two lines, the movement element being disposed outside the prop, and the control ends of the two lines are fixed to the movement element.

BRIEF DESCRIPTION OF THE DRAWINGS

The invention will be better understood after reading the following description, given purely by way of example and with reference to the attached drawings, in which.

DETAILED DESCRIPTION OF THE INVENTION

The device illustrated in FIGS. 1 to 5 includes a tubular endoprosthesis 11 mounted in a coaxial manner on a single prop 13 and connected to the prop 13 by releasable retaining means.

The endoprosthesis 11 comprises a tubular stainless steel mesh which has resilient properties. The endoprosthesis is thus self-expandable.

As is known per se, the endoprosthesis 11 can spontaneously deform from a compressed state, in which it has a small diameter (FIG. 1), to an expanded state, in which it has a greater diameter (FIG. 5), the expanded state being its rest state.

At a distal end 15 of the endoprosthesis, the mesh has wires doubled over to form loops 17.

Figure 1:
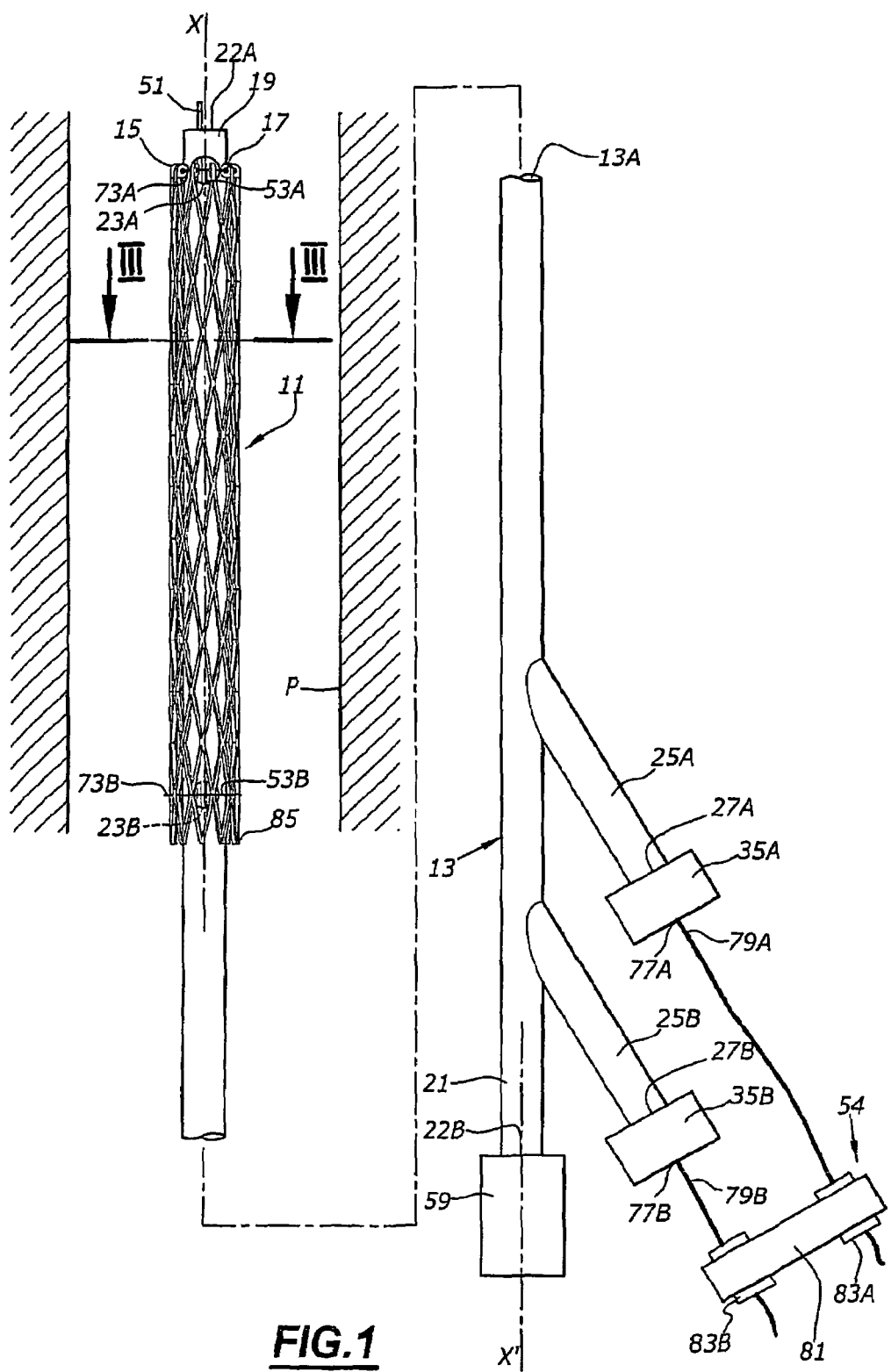
FIG. 1 is an elevated view of a first treatment device according to the invention.
Figure 2:
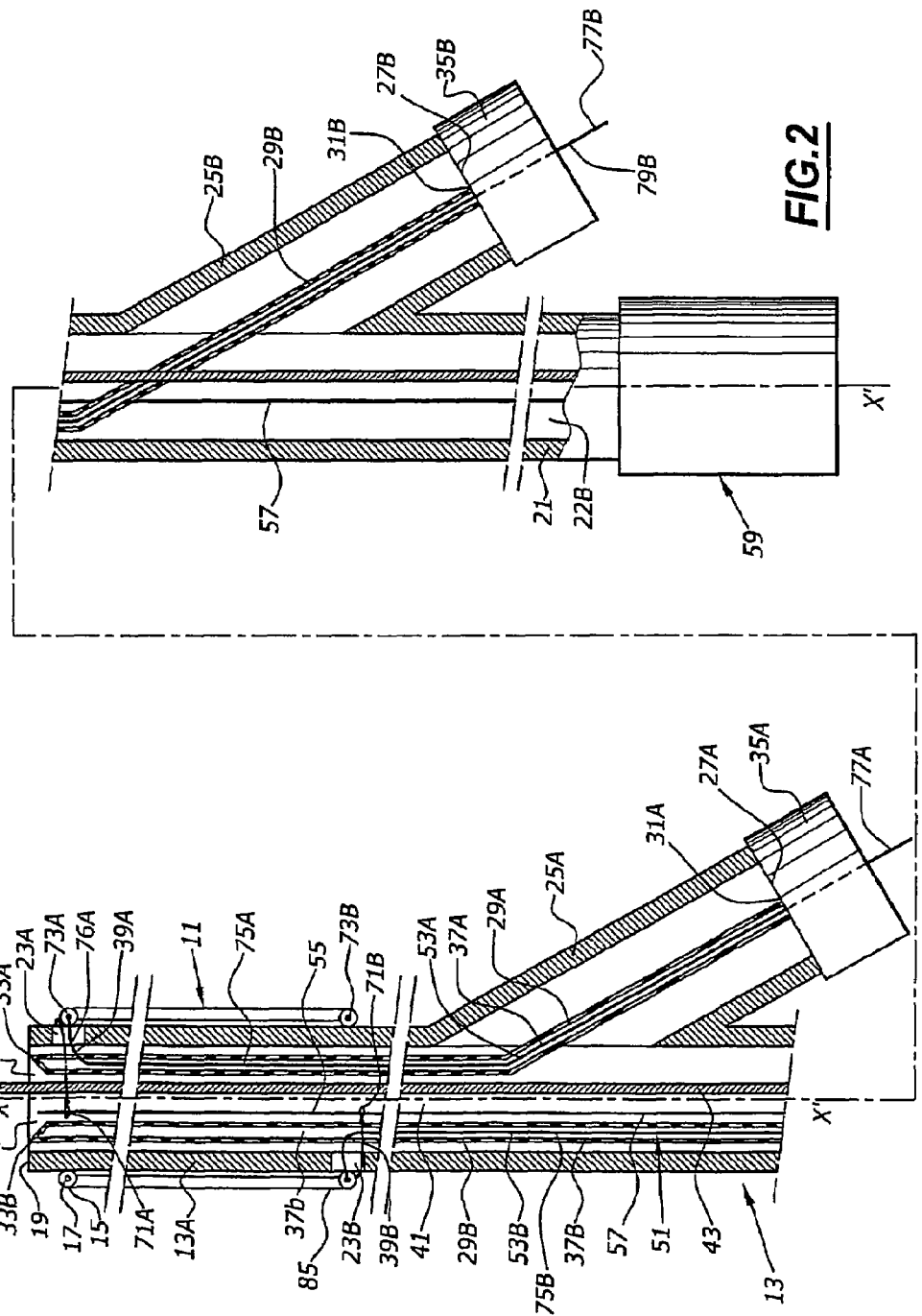
FIG. 2 is an enlarged partial sectional view following a medial longitudinal plane of the device in FIG. 1.

In the embodiment illustrated in FIGS. 1 and 2, the prop 13 comprises a hollow, resilient, wire tubular wall 13A which delimits a central passage 14.

The prop 13 extends longitudinally along a longitudinal axis X-X' between a distal end 19 for implantation in the blood vessel and a proximal end 21 which provides access for a surgeon.

At the distal and proximal ends 19, 21 of the prop 13 there are respective passage openings 22A, 22B of axis X-X' which open into the central passage 14. The distal and proximal retaining openings 23A and 23B, which are longitudinally offset, are arranged laterally in the prop 13. In this embodiment, the openings 23A and 23B are arranged on opposite sides with respect to a medial longitudinal plane of the prop 13. The distance separating the distal retaining opening 23A from the proximal retaining opening 23B is substantially equal to the length of the endoprosthesis 11 in its retracted state, taken in a longitudinal direction.

In addition, the prop 13 comprises distal and proximal hollow branches 25A, 25B in the vicinity of its proximal end 21. The branches 25A and 25B are longitudinally offset along the prop 13 and connect to the passage 14 inside the prop 13. A control passage 27A, 27B is provided at a free end of each branch 25A, 25B.

As illustrated in FIG. 2, the prop 13 comprises, for each retaining opening 23A, 23B, an internal insulating duct 29A, 29B for insulating the retaining means releasably connected to a respective branch 25A, 25B. The insulating ducts 29A, 29B are made from a resilient self-supporting plastics material. They are formed by tubes with a cylindrical cross-section. Each insulating duct 29A, 29B extends longitudinally in the central passage 14 between a proximal end 31A, 31B engaged in the control passage 27A, 27B and a distal end 33A, 33B arranged at the distal end 19 of the prop in the passage 14. The proximal end 31A, 31B of each insulating duct 29A, 29B is fitted with a stopper 35A, 35B for sealing the control passage 27 screwed onto the corresponding branch 25A, 25B. Each insulating duct 29A, 29B is sealed at its distal end 33A, 33B, thus forming a bevel which extends towards the distal end of the prop 13. The ducts 29A, 29B internally delimit channels 37A, 37B for receiving the releasable retaining means.

Each insulating duct 29A, 29B defines a distal passage 39A, 39B which extends longitudinally substantially opposite an associated retaining opening 23A, 23B and which opens out into the channel 37A, 37B. Each insulating duct 29A, 29B is thus fixed to the prop 13 by its proximal end 31A, 31B, but remains free at its distal end 33A, 33B. In a variant, each duct 29A, 29B is also fixed to the prop 13 at its distal end 33A, 33B by an adhesive point.

Figure 3:
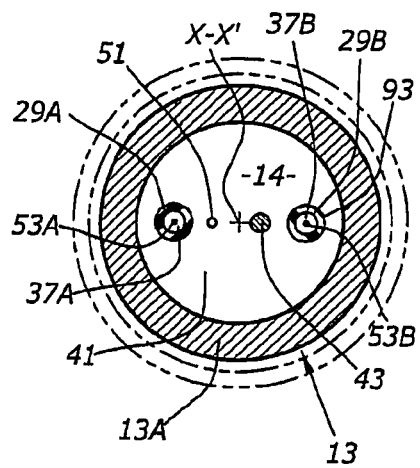
FIG. 3 is an enlarged partial cross-section following a transverse plane III-III of a detail in FIG. 1.

As illustrated in FIG. 3, each channel 37A, 37B has a cylindrical transverse cross-section which extends over part of a circumference surrounding axis X-X' of the central passage 16. In the example shown, the ducts 29A, 29B are arranged on the same circumference surrounding the longitudinal axis X-X'. Furthermore, each channel 37A, 37B extends radially in transverse cross-section over part of the distance which separates axis X-X' and the tubular wall 13A.

As illustrated in FIG. 3, the space in the passage 14 between the insulating ducts 29A, 29B and the wall 13A forms a guiding duct 41 for moving and guiding a surgical guide 43. The insulating ducts 29A and 29B are disposed at the periphery of the guiding duct 41.

The releasable device for retaining the endoprosthesis 11 comprises a retaining rod 51, distal and proximal retaining wires 53A and 53B, and a bar 54 for controlling the retaining wires.

The retaining rod 51 is disposed in the central passage 14. The length of the rod 51 is greater than or equal to the distance between the distal retaining opening 23A and the proximal end 21 of the prop 13. As illustrated in FIG. 2, the rod 51 comprises an active part 55 arranged in the vicinity of the distal end 19 and an operating part 57 which extends as far as the proximal end 21 of the prop 13.

The rod 51 can move in translation inside the prop 13 between a retaining position in which the active part 55 of the rod is opposite the two retaining openings 23A and 23B, an intermediate position in which the active part 55 is opposite the proximal retaining opening 23B and away from the distal retaining opening 23A, and a release position in which the active part 55 is away from the two retaining openings 23A and 23B.

The rod 51 is fixed to the proximal end 21 of the prop 13 by a removable stopper 59 which seals the proximal passage opening 22B.

Figure 4:
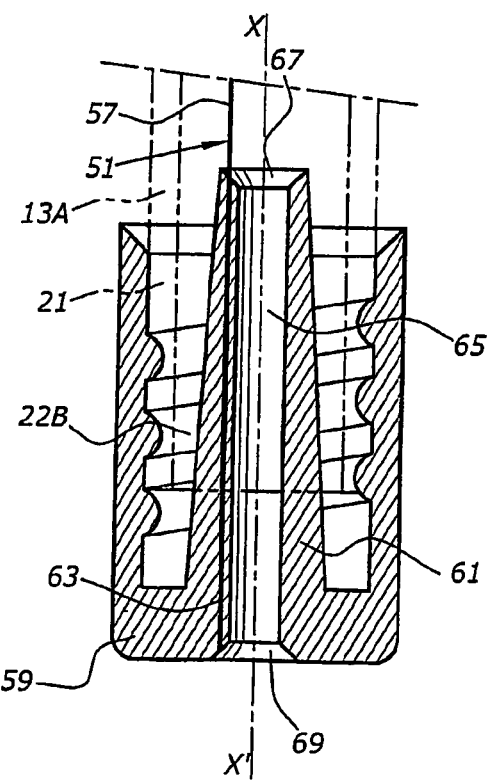
FIG. 4 is a detailed view of FIG. 2.

As illustrated in FIG. 4, the stopper 59 has a central sleeve 61 of axis X-X'. The proximal base 63 of the rod 51 is embedded in a wall of the sleeve 61 in such a way that the rod 51 is axially offset with respect to axis X-X'. The sleeve 61 delimits a central channel 65 of axis X-X' which provides a distal entrance 67 into the central passage 14 and a proximal entrance 69 outside the prop 13. The distal entrance 67 is delimited by a distally diverging (outwardly flared) surface of the sleeve 61, and the proximal entrance 69 is delimited by a surface of the prop 13 diverging towards the exterior.

In the example illustrated in FIGS. 1 to 5, each retaining wire 53A, 53B comprises only one strand which includes an end eyelet 71A, 71B, a tightening loop 73A, 73B and a control portion 75A, 75B.

In a variant (not illustrated), each retaining wire 53A, 53B comprises two parallel strands connected to one another at least by an end part. The eyelet is formed directly by means of the end part, engaged around the rod 51.

The end eyelet 71A, 71B is formed at a distal end of the strand. It is formed of a closed loop with a small diameter. The active part 55 of the rod 51 is engaged in the eyelet 71A, 71B when the rod 51 is in its retaining position. The eyelet 71A, 71B can also be deformed in such a way that its size, when it is deformed, is substantially equal to double the size of the strand. This size is smaller than the internal diameter of the loops 17. The eyelet 71A, 71B is connected to the tightening loop 73A, 73B by a section 76A engaged in the corresponding retaining opening 23A, 23B.

In the example illustrated in FIG. 1, the tightening loop 73A, 73B is formed by a strand portion, slidingly engaged in the end loops 17 of the mesh of the endoprosthesis 11, following a circumference of the endoprosthesis 11, surrounding a longitudinal axis. Each tightening loop 73A, 73B fixes the endoprosthesis 11 to the prop 13. Furthermore, the active length of the tightening loop 73A, 73B can be varied in such a way that it controls deployment of the endoprosthesis 11 with respect to the prop 13 as described hereinafter.

As illustrated in FIG. 2, each control portion 75A, 75B extends into an insulating duct 29A, 29B between its distal passage 39A, 39B and the control passage 27A, 27B of the corresponding control branch 25A, 25B. Each insulating duct 29A, 29B thus receives only one control portion 75A, 75B which is insulated by the duct 41. As a result, the duct 41 for moving the guide 43 in the central passage 14 has no retaining wire 53A, 53B between the proximal end 21 of the prop and the proximal retaining opening 23A, thus allowing the guide 43 to be moved without mechanically interacting with the wires 53A, 53B.

A control end 77A, 77B of the control portion 75A, 75B is engaged across the control passage 27A, 27B. Thus, a part 79A, 79B of the portion projects outside the branch 25A, 25B through the stopper 35A, 35B. The length of the projecting part 79A, 79B is variable and controls the length of the tightening loop 73A, 73B.

Hence, an increase in the length of the projecting part 79A, 79B causes displacement of the control portion 75A, 75B with respect to the prop 13 towards the proximal end 21 of the prop, as well as a corresponding decrease in the active length of the tightening loop 73A, 73B. As a result, the endoprosthesis 11 is clamped against the prop 13 at the tightening loop 73A, 73B. When the endoprosthesis 11 is in its retracted state against the prop 13, the control portion 75A, 75B is in a drawn position.

Conversely, a decrease in the length of the projecting part 79A, 79B causes displacement of the control portion 75A, 75B with respect to the prop 13 towards the distal end 19 of the prop 13, as well as an increase in the active length of the tightening loop 73A, 73B and, as a result, deployment of the endoprosthesis 11 at a distance from the prop 13, at the tightening loop 73A, 73B. When the endoprosthesis 11 is in its expanded state, the control portion 75A, 75B is in a relaxed position.

Each stopper 35A, 35B comprises a diametrically adjustable central opening in which the projecting part 79A, 79B is engaged. By setting the diameter of the central opening of the stopper 35A, 35B, the projecting part 79A, 79B of the control portion 75A, 75B is selectively immobilized with respect to the prop 13 and the length of the projecting part 79A, 79B is fixed. As a result, the active length of the tightening loop 73A, 73B is also fixed.

The control bar 54 comprises a grip 81 and fasteners 83A, 83B for releasably fixing the ends of the control portions 75A, 75B arranged on both sides of the grip. The grip 81 is arranged outside the passage 14 at a distance from the prop 13. The free ends of the control portions 75A, 75B at the projecting parts 79A, 79B are fixed respectively on both sides of the grip 81 of the bar 54. The bar 54 allows single-handed simultaneous operation of the two control wires 53A, 53B, as will be shown hereinafter.

By way of example, the operation of the first treatment device according to the invention will now be described.

Figure 5:
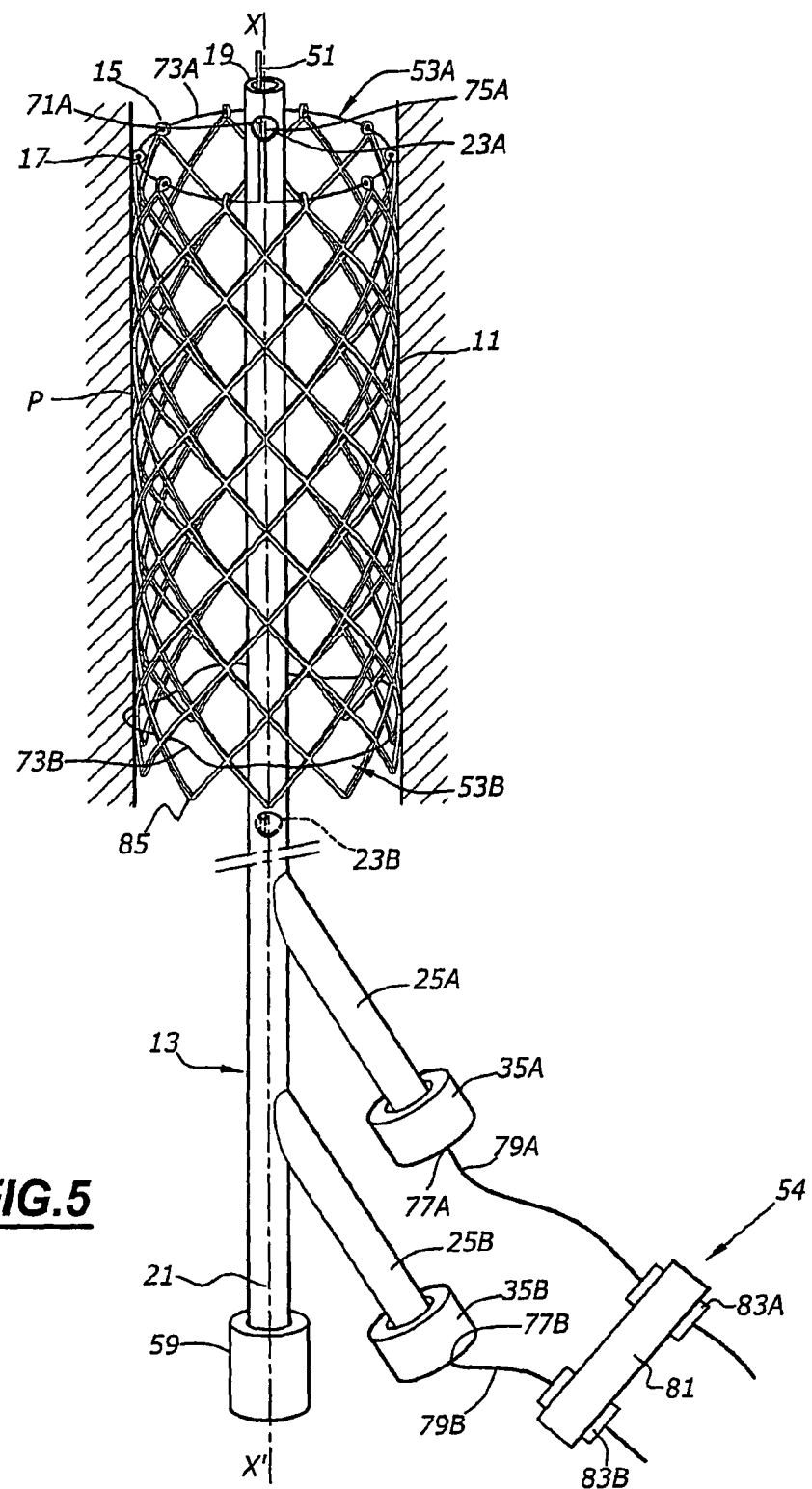
FIG. 5 is a view similar to FIG. 1, the endoprosthesis being deployed in a reversible manner.

In a first phase, the device is packaged (not shown) with the endoprosthesis 11 in a deployed state similar to that shown in FIG. 5. In this configuration, the control rod 51 is in its retaining position. The distal and proximal retaining wires 53A and 53B are engaged in the rod 51 and in the mesh of the endoprosthesis 11. This encapsulation retains the mechanical properties of the endoprosthesis 11, in particular when the tubular mesh of the endoprosthesis is embedded in an expandable film, such as an elastomer, which is impervious to liquids.

In a second phase, the surgeon takes the device out of its packaging. He implants the surgical guide 43 extending in the blood vessel or the vein from the outer insertion point as far as the region of the vein or the artery in which the tubular endoprosthesis is to be implanted.

In a third phase, in view of the implantation of the endoprosthesis 11 in the blood vessel or vein, the surgeon simultaneously operates the retaining wires 53A and 53B by pulling the grip 81 away from the prop 13 so as to increase the length of the projecting part 79A, 79B of the control portion 75A, 75B. Thus, he simultaneously displaces the control portions 75A, 75B towards the proximal end 21 of the prop 13. The active length of each tightening loop 73A, 73B decreases in such a way that the endoprosthesis 11 is retracted against the prop 13 and securely fixed with respect thereto.

In certain cases and in order to maintain minimal radial dimensions, a sheath (not shown) is disposed around the endoprosthesis 11 before the insertion and is withdrawn once insertion has taken place.

The endoprosthesis 11 is then in the retracted state illustrated in FIG. 1 in which the mesh substantially rests against the prop 13. The endoprosthesis is thus inserted as far as its place of implantation by displacement along the surgical guide 43. To achieve this, the guide 43 is inserted into the central passage 14 by opening the distal passage 22A. The insertion of the guide 43 inside the passage 14 is facilitated by the bevelled shape of the distal ends of the ducts 29A, 29B. Furthermore, since the control portions 75A, 75B of the wires 53A, 53B are disposed in the ducts 29A, 29B, the guide 43 is free to move in the duct 41 without coming into contact with wires 53A, 53B (i.e., the guide 43 can contact the outer surface 93 of each insulating duct 29A, 29B, but the guide 43 cannot penetrate through the ducts 29A, 29B to contact wires 53A, 53B within the ducts 29A, 29B).

When the end of the guide 43 reaches the proximal end 21 of the prop, the guide 43 penetrates the central channel 65 of the stopper 59. The diverging shape of the sleeve 61 at the entrance 67 also allows easy guiding of the guide 43. The prop bearing the endoprosthesis is then displaced along the guide 43.

Once the endoprosthesis 11 has been inserted, the surgeon proceeds with deployment thereof. Depending on the size of the vessel to be treated, the surgeon may choose to deploy either end of the endoprosthesis 11 first. By way of example, deployment of the distal end 15 will now be described.

First of all, the surgeon progressively decreases the length of the projecting part 79A of the control portion 75A by releasing the part from the stopper 35A. He displaces the control portion 75A towards the distal end 19 of the prop 13 with the aid of the bar 54. As a result, the active length of the tightening loop 73A increases.

The mesh of the endoprosthesis 11 thus deforms spontaneously from the compressed state shown in FIG. 1 to the deployed state shown in FIG. 5. During this deformation, the end loops 17 of the mesh move away from the prop 13 and move closer to the walls P of the vessel to be treated in order to come into contact with the walls P. In a similar manner, the surgeon then effects deployment of the proximal end 85 of the endoprosthesis by the proximal retaining wire 53B (FIG. 5).

Being insulated from one another in each insulating duct 29A, 29B, the control portions 75A, 75B are reliably displaced and the risk of the wires 53A, 53B being blocked is largely reduced.

When the surgeon is satisfied with the positioning of the distal end 15 of the endoprosthesis 11, he moves the retaining rod 51 from its retaining position to the intermediate position.

During this movement, the eyelet 71A of the distal retaining wire 53A is released from the rod 51. The surgeon then pulls the control end 77A with the aid of the bar 54 in order to lead the distal end of the distal retaining wire 23A to the control passage 27, then through the loops 17 of the mesh of the endoprosthesis 11, the inside of the prop 13, and the control branch 25A.

In a variant, the control portions 75A, 75B of the retaining wires 53A, 53B are simultaneously released from their stoppers 35A, 35B. The surgeon then simultaneously manoeuvres the two control portions 75A, 75B with the aid of the grip 81 of the bar. As a result, he can simultaneously deploy the two ends 15, 85 of the endoprosthesis 11 by displacing the two ends 83A, 83B of the grip 81 towards the stoppers 35A, 35B. He may also deploy one of the ends 15, 85 of the endoprosthesis by keeping the other end of the endoprosthesis retracted against the prop 13 by displacing only one of the ends 83A, 83B of the grip 81 towards the associated stopper 35A, 35B.

The bar 54 thus facilitates the handling of the device and allows the surgeon to single-handedly select either deployment or retraction of one and/or the other of the ends of the endoprosthesis 11.

Figure 6:
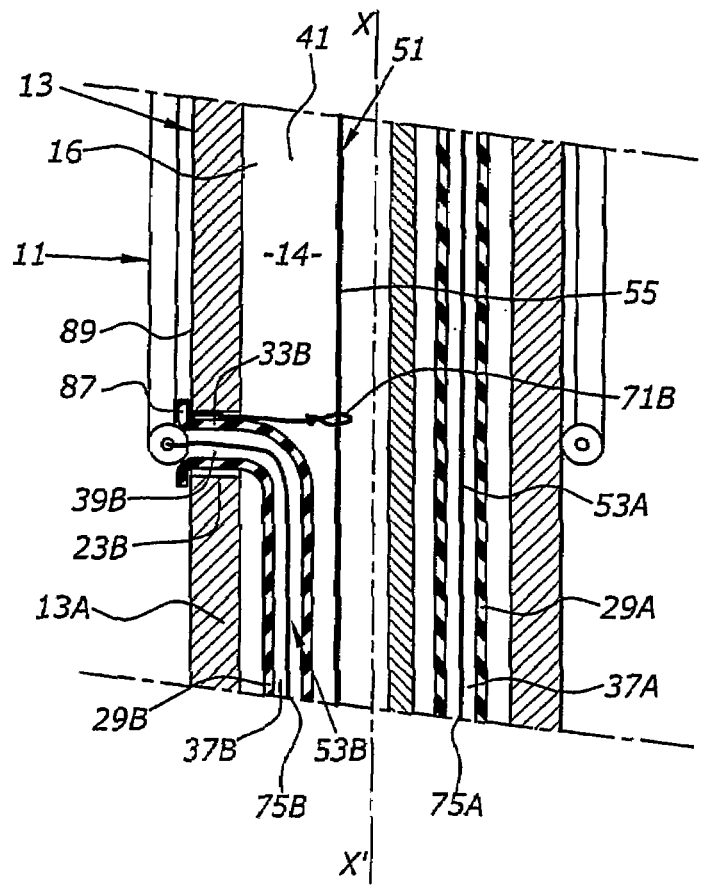
FIG. 6 is a partial cross-section following a medial longitudinal plane of a second device according to the invention.

In the second device according to the invention, shown in part in FIG. 6, the distal passage 39B is arranged at the distal end 33B of the insulating duct 29B. Around the passage 39B at its distal end 33B, the insulating duct 29B also has a collar 87 for application on the wall 13A of the prop. The duct 29B is bent in the vicinity of its distal end 33B which is engaged through the retaining opening 23B. The collar 85 rests upon an external surface 89 of the prop 13 surrounding the opening 23B and fixes the duct 29B to the prop 13.

Figure 7:
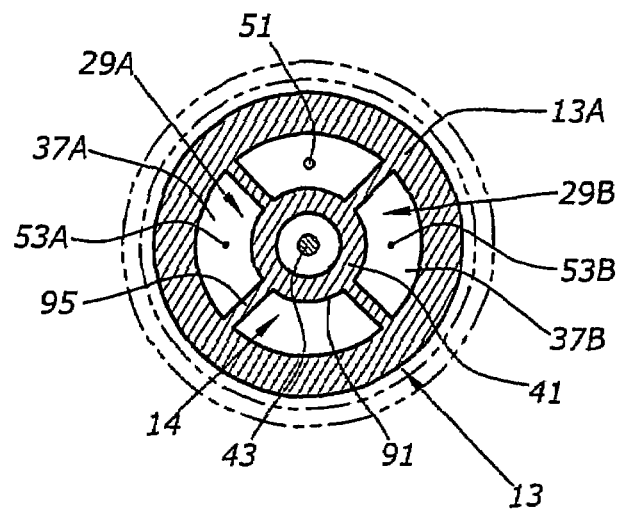
FIG. 7 is a view similar to FIG. 3 of a third device according to the invention.

In the third device according to the invention, shown in FIG. 7, the prop 13 comprises a central duct 91 for moving the guide formed by a tubular part of axis X-X' disposed in the central passage 14 and extending as far as the proximal end 21 of the prop. The central duct 91 is connected to the wall 13A of the prop 13 by plane axial walls 95. The axial walls 95 have a transverse cross-section extending radially away from axis X-X'. They delimit, between the central duct 91 and the wall 13A, a plurality of insulating ducts 29A, 29B which receive the retaining wires 53A, 53B. The duct 91, the wall 13A, and the walls 95 are integral, the prop 13 being able to be produced, for example, by extrusion.

Each channel 37A, 37B thus has a transverse cross-section in the shape of a truncated angular section which covers part of the annular surface extending between the duct 91 and the wall 13A of the prop around axis X-X'. The angle formed by two adjacent axial walls 95 is, for example, between 10 and 150°.

Figure 8:
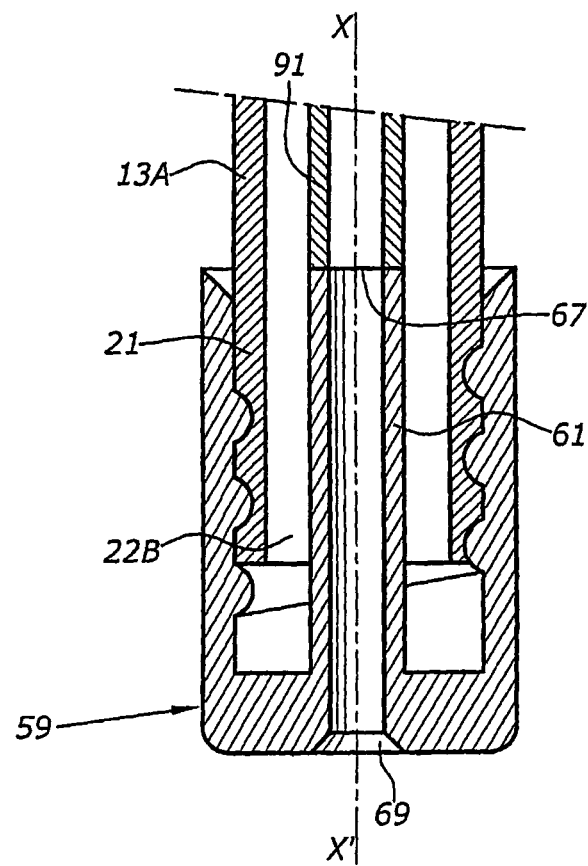
FIG. 8 is a view similar to FIG. 4 of the third device according to the invention.

As shown in FIG. 8, the stopper 59 is formed in such a way that the internal surface of the sleeve 61 is internally flush with the internal surface of the duct 91 in order to facilitate the passage of the guide between the duct 91 and the stopper 59.

Owing to the invention which has just been described, it is possible to provide a device for treating a blood vessel which is easily inserted on a surgical guide 43. The device is therefore placed precisely in a blood vessel. Since the releasable retaining wires 53A, 53B of the endoprosthesis 11 are disposed in the insulating ducts 29A, 29B, the risk of mechanical interaction between said wires 53A, 53B and the guide 43 is largely reduced. Furthermore, the movement of the control portions 75A, 75B of the wires is rendered extremely reliable thanks to their arrangement in the internal insulating ducts 29A, 29B.

The use of a bar 54 connecting the free ends of the control portions 75A, 75B of the retaining wires 53A, 53B of the endoprosthesis considerably simplifies operation of the device and facilitates use thereof using just one hand. It will be noted that the bar 54 applies to other types of devices for deploying medical implants comprising at least two control wires, in particular those with no insulating ducts 29 as disclosed in application FR 2 863 160.

The presence of diverging surfaces at the ends 19, 21 of the prop 13 facilitates insertion of the guide 43 into the central passage 14, either from the distal end towards the proximal end of the prop 13 or the other way round.

The invention claimed is:

1. A device for treating a blood vessel, comprising:
   an implant deployable between a contracted state and an expanded state;
   a hollow prop having a proximal end and a distal end and internally delimiting a central passage between said proximal end and said distal end, said hollow prop having a retaining opening at said distal end for retaining said implant, said prop having a length longer than a length of said implant;
   at least one filamentary line for releasably fixing said implant to said prop, each of said at least one filamentary line having a pulling portion extending through said retaining opening and into said central passage, and each of said at least one filamentary line having a control portion extending from said pulling portion to said proximal end of said prop for providing control of each of said at least one filamentary line; and
   at least one tubular-shaped internal insulating duct arranged within said central passage of said prop and axially fixed to said prop, only one of said at least one filamentary line being received within and extending through a respective one of said at least one insulating duct such that each of said at least one insulating duct receives only one filamentary line, a guiding duct being defined within said central passage of said prop between said at least one insulating duct and a wall of said prop, and having no filamentary line outside of said at least one insulating duct.

2. The device of claim 1, wherein each of said at least one tubular-shaped insulating duct has a cylindrical cross section.

3. The device of claim 1, wherein said at least one filamentary line comprises a first filamentary line and a second filamentary line for releasably fixing said implant to said prop, said at least one tubular-shaped insulating duct comprising a tubular-shaped first insulating duct and a tubular-shaped second insulating duct, only said first filamentary line being received within and extending through said first insulating duct, and only said second filamentary line being received within and extending through said second insulating duct, wherein each of said first insulating duct and said second insulating duct receives only one filamentary line therein.

4. The device of claim 1, wherein each of said at least one tubular-shaped insulating duct comprises a channel for receiving one of said at least one filamentary line, said channel extending in cross-section over part of a circumference of said prop surrounding a longitudinal axis X-X' of said central passage.

5. The device of claim 1, wherein each of said at least one tubular-shaped insulating duct has a distal passage extending substantially opposite said retaining opening, a respective one of said at least one filamentary line being engaged in said distal passage of each of said at least one tubular-shaped insulating duct.

6. The device of claim 1, wherein each of said at least one insulating duct has a sealed distal end with a beveled shape.

7. The device of claim 1, wherein each of said at least one tubular-shaped insulating duct extends into said retaining opening, each of said tubular-shaped insulating duct comprising a collar sitting against an external surface of said prop, said collar delimiting a distal passage.

8. The device of claim 1, wherein each of said at least one tubular-shaped insulating duct is integral with said prop over substantially an entire length of said at least one tubular-shaped insulating duct.

9. The device of claim 1, wherein each of said at least one tubular-shaped insulating duct is integral with said prop.

10. The device of claim 1, wherein said prop comprises a proximal passage opening and a distal passage opening substantially coaxial with each other, said guiding duct extending between said proximal passage opening and said distal passage opening, said prop having a distally diverging surface delimiting said guiding duct at at least one of said proximal passage opening and said distal passage opening.

11. The device of claim 1, wherein said at least one filamentary line comprises at least two filamentary lines, said at least one insulating duct comprising at least two insulating ducts associated with said at least two filamentary lines such that only one of said at least two filamentary lines extends within a respective one of said at least two insulating ducts, wherein each of said at least two insulating ducts receives only one of said at least two filamentary lines therein, and wherein said at least two insulating ducts are arranged at a periphery of said guiding duct.

12. The device of claim 11, wherein said prop has at least two retaining openings longitudinally spaced along a longitudinal axis of said prop.

13. The device of claim 11, further comprising a movement element configured to jointly move said at least two filamentary lines, said movement element being located outside of said prop, said respective control portions of said at least two filamentary lines are fixed to said movement element.

14. The device of claim 1, further comprising a retaining rod extending through said central passage of said prop outside of each of said at least one tubular-shaped insulating duct.

15. The device of claim 14, wherein said central passage is configured to allow a surgical guide to extend therethrough outside of each of said at least one tubular-shaped insulating duct.

16. The device of claim 1, wherein said central passage is configured to allow a surgical guide to extend therethrough outside of each of said at least one tubular-shaped insulating duct.

* * * * *